United States Patent
Tsunoda et al.

(10) Patent No.: US 6,911,566 B2
(45) Date of Patent: Jun. 28, 2005

(54) PROCESS FOR PRODUCING 1,3-PROPANEDIOL

(75) Inventors: Takashi Tsunoda, Kurashiki (JP); Kouji Nomura, Kurashiki (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 0 days.

(21) Appl. No.: 10/469,513

(22) PCT Filed: Mar. 1, 2002

(86) PCT No.: PCT/JP02/01921

§ 371 (c)(1),
(2), (4) Date: Sep. 2, 2003

(87) PCT Pub. No.: WO02/070447

PCT Pub. Date: Sep. 12, 2002

(65) Prior Publication Data

US 2004/0097764 A1 May 20, 2004

(30) Foreign Application Priority Data

| | | |
|---|---|---|
| Mar. 2, 2001 | (JP) | 2001-057877 |
| Mar. 16, 2001 | (JP) | 2001-075408 |
| Dec. 21, 2001 | (JP) | 2001-389260 |

(51) Int. Cl.⁷ .................. C07C 31/20; C07C 31/18; C07C 29/241; C07C 29/14
(52) U.S. Cl. .................. 568/862; 568/449; 568/496; 568/852; 568/861; 568/857
(58) Field of Search .................. 568/862, 852, 568/861, 857, 449, 496

(56) References Cited

U.S. PATENT DOCUMENTS

| | | |
|---|---|---|
| 2,434,110 A | 1/1948 | Hatch et al. |
| 3,536,763 A | 10/1970 | Eleuterio et al. |
| 5,093,537 A | 3/1992 | Unruh et al. |
| 5,171,898 A | 12/1992 | Arntz et al. |
| 5,276,201 A | 1/1994 | Haas et al. |
| 6,140,543 A | 10/2000 | Brossmer et al. |

FOREIGN PATENT DOCUMENTS

| | | |
|---|---|---|
| EP | 0 487 903 A2 | 6/1992 |
| EP | 0 544 120 A1 | 6/1993 |

*Primary Examiner*—Elvis O. Price
(74) *Attorney, Agent, or Firm*—Birch, Stewart, Kolasch & Birch, LLP

(57) ABSTRACT

A process for producing 1,3-propanediol, comprising:

hydrating acrolein in a liquid phase in the presence of a hydration catalyst to form 3-hydroxypropanal;

separating any unreacted acrolein, if any is present; and carrying out catalytic hydrogenation of the 3-hydroxypropanal in a liquid or gas phase with a hydrogenation catalyst, wherein the hydration catalyst is a catalyst comprising at least one member selected from the group consisting of the following materials (a) to (c) and has a pH of 6 or less at 20° C., when made into a slurry by dispersing the catalyst in a quantity of water 5 times as much as the quantity of catalyst by weight:

(a) a metalloaluminophosphate molecular sieve, (b) an FER type zeolite, and (c) an oxide or compound oxide, excluding crystalline aluminosilicate zeolites, which comprises one or more element(s) selected from the elements belonging to group 4, group 13 and group 14 of the periodic table.

13 Claims, No Drawings

PROCESS FOR PRODUCING 1,3-PROPANEDIOL

This application is the national phase under 35 U.S.C. § 371 of PCT International Application No. PCT/JP02/01921 which has an International filing date of Mar. 1, 2002, which designated the United States of America, which also claims foreign priority under 35 USC 119 to Application No. 2001-057877 filed in Japan on Mar. 2, 2001, Application No. 2001-075408 filed in Japan on Mar. 16, 2001 and Application No 2001-389260 filed in Japan on Dec. 21, 2001. The entire contents of all of the above applications are hereby incorporated by reference.

TECHNICAL FIELD

The present invention relates to a process for producing 1,3-propanediol by hydrating acrolein with water in the presence of a solid acid catalyst to produce 3-hydroxy-propanal, and then subjecting the 3-hydroxypropanal to catalytic hydrogenation.

BACKGROUND ART 1,3-Propanediol is an important chemical starting material that is potentially usable in various fields as a starting monomer for polyester and polyurethane and a starting material for synthesizing cyclic compounds.

It is known that hydration of acrolein with water in the presence of an acid catalyst yields 3-hydroxy-propanal (3-hydroxypropionaldehyde, hereinafter abbreviated as 3-HPA) and that subsequent hydrogenation of 3-HPA in the presence of a conventional hydrogenation catalyst yields 1,3-propanediol.

The specification of U.S. Pat. No. 2,434,110 discloses a process for producing 3-HPA by hydrating acrolein in the presence of an acid catalyst. In this process, an acid (e.g. sulfuric acid, phosphoric acid, oxalic acid, an acid salt or acetic acid) uniformly dissolved in an aqueous acrolein solution is used as the catalyst. In this process, sulfuric acid is preferably used and the yield of 3-hydroxypropionaldehyde is low because a condensation reaction proceeds simultaneously with the hydration. The hydration products including 3-HPA are hydrogenated in the presence of a conventional hydrogenation catalyst, if necessary, after the unreacted acrolein is removed therefrom. As the hydrogenation catalyst for converting 3-HPA to 1,3-propanediol, a catalyst containing one or more metals having hydrogenating activity, such as Ni, Fe, Co, Cu, Ag, Mo, W, V, Cr, Rh, Pd, Pt, Ir, Os, etc. is used. Since the hydrogenation reaction of 3-HPA into 1,3-propanediol proceeds very selectively, improving the selectivity of the hydration reaction of acrolein is important for obtaining 1,3-propanediol from acrolein in a high yield.

Therefore, methods for improving the selectivity of the hydration reaction of 2-alkenal, in particular, processes using a solid acid catalyst have been proposed. There have been disclosed, for example, a process using a weakly acidic cation-exchange resin catalyst (U.S. Pat. No. 3,536,763), a process using a chelate-forming ion-exchange resin catalyst (European Patent Application Laid-Open No. 0487903), a process using hydrated alumina-bound zeolite with a pore size of 5 angstrom or more as a catalyst (JP-A-5-194291 and European Patent Application Laid-Open No. 0524713), and a process using a catalyst supporting a polyacid with a first $pk_s$ value of 0 to 3 (JP-A-5-221912 and European Patent Application Laid-Open No. 0544120).

However, although the selectivity of the hydration reaction of acrolein into 3-HPA has been improved in the above conventional processes as compared with the technique described in the specification of U.S. Pat. No. 2,434,110 which uses a homogeneous catalyst system, the selectivity is still insufficient and a production process having a higher selectivity is desired.

Accordingly, the object of the present invention is to provide an improved process for producing 1,3-propanediol by hydrating acrolein in the presence of a hydration catalyst to produce 3-hydroxypropanal and then subjecting the 3-hydroxypropanal to catalytic hydrogenation, which makes it possible to obtain 3-hydroxypropanal with high selectivity.

SUMMARY OF THE INVENTION

The present inventors earnestly investigated in order to solve the above problems, and consequently found that acrolein can be hydrated into 3-hydroxypropanal with high selectivity when a specific catalyst comprising one or more member(s) selected from a metalloalumino-phosphate molecular sieve, an FER type zeolite, and a specific oxide or compound oxide. On the basis of this finding, the present invention has been accomplished.

That is, the present invention comprises the following aspects 1) to 10).

1) A process for producing 1,3-propanediol, comprising:
hydrating acrolein in a liquid phase in the presence of a hydration catalyst to form 3-hydroxypropanal;
separating any unreacted acrolein, if any is present; and
carrying out catalytic hydrogenation of the 3-hydroxypropanal in a liquid or gas phase with a hydrogenation catalyst,
wherein the hydration catalyst is a catalyst comprising at least one member selected from the group consisting of the following materials (a) to (c) and has a pH of 6 or less at 20° C., when made into a slurry by dispersing the catalyst in a quantity of water 5 times as much as the quantity of catalyst by weight ratio:
(a) an metalloaluminophosphate molecular sieve,
(b) an FER type zeolite, and
(c) an oxide or compound oxide, excluding crystalline aluminosilicate zeolites, which comprises one or more element(s) selected from the elements belonging to group 4, group 13 and group 14 of the periodic table.

2) The process according to the above item 1), wherein the metalloaluminophosphate molecular sieve is a silicoaluminophosphate molecular sieve.

3) The process according to the above item 2), wherein the silicoaluminophosphate molecular sieve is SAPO-34.

4) The process according to the above item 2), wherein the silicoaluminophosphate molecular sieve is SAPO-11.

5) The process according to the above item 1), wherein the FER type zeolite is ferrierite.

6) The process according to the above item 1), wherein the oxide or compound oxide is one obtained by contacting with one or more acids selected from the group consisting of sulfuric acid and monobasic acids and then washing with water until the washings have become free of acid(s).

7) The process according to the above item 1) or 6), wherein the oxide is alumina.

8) The process according to the above item 1) or 6), wherein the metalloaluminophosphate molecular sieve is SAPO-34 or SAPO-11, the FER type zeolite is ferrierite, and the oxide is alumina.

9) The process according to any one of the above items 1) to 8), wherein the hydration reaction is carried out at a reaction temperature of 20 to 200° C. and a weight ratio of acrolein to water of 1:2 to 1:20.

10) The process according to any one of the above items 1) to 9), wherein the catalytic hydrogenation of the 3-hydroxypropanal is carried out at a temperature of 30–200° C. and a pressure of 1–20 MPa in the presence of a catalyst containing nickel or a noble metal.

PREFERRED EMBODIMENTS FOR CARRYING OUT THE INVENTION

In the production process of the present invention, as the hydration catalyst, a catalyst comprising at least one member selected from the group consisting of the following materials (a) to (c) is used, wherein the pH is 6 or less at 20° C., when made into a slurry by dispersing said catalyst in a quantity of water of 5 times as much as the quantity of catalyst by weight ratio:

(a) a metalloaluminophosphate molecular sieve, (b) an FER type zeolite, and (c) an oxide or compound oxide (excluding crystalline aluminosilicate zeolites), which comprises one or more elements selected from the elements belonging to group 4, group 13 and group 14 of the periodic table.

The metalloaluminophosphate molecular sieve used in the present invention is an aluminophosphate molecular sieve in which P or Al is partially replaced by one or more elements selected from the group consisting of Si, Mg, Mn, Co, Zn, Fe, Ti, B, Cr, Ga, Ge, Li and Ni. Specific examples thereof are the molecular sieves disclosed in, for example, the specifications of U.S. Pat. Nos. 4,440,871; 4,500,561; 4,567,029 and 4,554,143, European Patent Application Laid-Open Nos. 0,158,349, 0,158,976 and 0,159,624, and JP-A-2-184509. Of these molecular sieves, the Si-containing silicoaluminophosphate molecular sieves (hereinafter abbreviated as "SAPO-n") disclosed in the specification of U.S. Pat. No. 4,440,871 are especially preferred. Specific examples of SAPO-n include SAPO-5, SAPO-11, SAPO-16, SAPO-17, SAPO-20, SAPO-34, SAPO-35, SAPO-37, SAPO-40, SAPO-42, SAPO-44, SAPO-31 and SAPO-41. These examples of SAPO-n have a composition after synthesis represented by the following general formula when they are on an anhydrous basis, and they are characterized by the specific X-ray powder diffraction pattern described in the specification of U.S. Pat. No. 4,440,871:

mR:(Si$_x$Al$_y$P$_z$)O$_2$ wherein R denotes at least one organic template; m is 0.02–0.3; x, y and z denote the molar fractions of Si, Al and P, respectively; x+y+z=1; and x=0.01–0.98, y=0.01–0.6, z=0.01–0.52, preferably, x=0.02–0.25, y=0.37–0.6, z=0.27–0.49.

Of the examples of SAPO-n, SAPO-11 and SAPO-34 are more preferred, and SAPO-34 is especially preferred. The X-ray powder diffraction patterns characterising SAPO-11 and SAPO-34 are shown in Table III and Table XI, respectively, in the specification of U.S. Pat. No. 4,440,871. Tables 1 and 2 show the characteristic X-ray powder diffraction patterns of SAPO-34 and SAPO-11, respectively. As to the relative intensity in the tables, W (weak), M (medium), S (strong) and VS (very strong) indicate that the intensity increases in that order.

TABLE 1

Characteristic X-ray powder diffraction pattern of SAPO-34

| 2θ (°) | Interplanar spacing (Å) | Relative intensity |
|---|---|---|
| 9.45–9.65 | 9.36–9.17 | S–VS |
| 16.0–16.2 | 5.54–5.47 | W–M |
| 17.85–18.15 | 4.97–4.89 | W–S |
| 20.55–20.9 | 4.32–4.25 | M–VS |
| 24.95–25.4 | 3.57–3.51 | W–S |
| 30.5–30.7 | 2.931–2.912 | W–S |

(X-ray source: Kα-ray of copper)

TABLE 2

Characteristic X-ray powder diffraction pattern of SAPO-11

| 2θ (°) | Interplanar spacing (Å) | Relative intensity |
|---|---|---|
| 9.4–9.65 | 9.41–9.17 | M |
| 20.3–20.6 | 4.37–4.31 | M |
| 21.0–21.3 | 4.23–4.17 | VS |
| 22.1–22.35 | 4.02–3.99 | M |
| 22.5–22.9 (double peak) | 3.95–3.92 | M |
| 23.15–23.35 | 3.84–3.81 | M–S |

(X-ray source: Kα-ray of copper)

The metalloaluminophosphate molecular sieve used in the present invention comprises Al, P, O and at least one of the other elements (M) selected from the above-mentioned group consisting of Si, Mg, Mn, Co, Zn, Fe, Ti, B, Cr, Ga, Ge, Li and Ni. In this molecular sieve, the (P$_2$O$_5$+Al$_2$O$_3$)/M molar ratio is preferably 1–300, more preferably 2–30. It is advantageous that the primary-particle size of crystals of said molecular sieve is small. When the volumes of particles of the crystals are converted to those of spherical particles, the average diameter of the spherical particles is preferably 2 μm or less, more preferably 0.5 μm or less.

Although the metalloaluminophosphate molecular sieve used in the present invention can be used after being washed, dried and then calcined in an inert gas atmosphere of air, nitrogen or the like after its synthesis, it is preferably used after being converted to H form (proton form) by ion exchange. Although there are various methods for the conversion to H form by ion exchange, said molecular sieve may be dissolved when subjected to ion exchange with a strong acid. Therefore, preferably, said molecular sieve is dispersed in an aqueous solution of an ammonium salt such as ammonium nitrate or ammonium chloride to obtain a slurry, after which the slurry is stirred at a room temperature or at 100° C. or lower for several hours to convert the molecular sieve to NH$_4$ form (ammonium ion form) by ion exchange, and the NH$_4$ form molecular sieve is filtered, washed and then calcined in an inert gas atmosphere of air, nitrogen or the like.

Specific examples of the FER type zeolite used in the present invention are natural or synthetic ferrierite, FU-9 (European Patent Application Laid-Open No. 55,529), ISI-6 (U.S. Pat. No. 4,578,259), NU-23 (European Patent Application Laid-Open No. 103,981), Sr-D (J. Chem. Soc., 2296–2305 (1964)) and ZSM-35 (U.S. Pat. No. 4,016,245). Of these, ferrierite is especially preferred. The entrance of pore of ferrierite is a 4.2 Å×5.4 Å oval and its effective pore size is about 4.5 Å. Ferrierite has a smaller pore size than the zeolites disclosed in the above reference JP-A-5-194291, i.e., ZSM-5 (pore size: about 5.8 Å), synthetic mordenite (pore size: about 7.8 Å) and Y-zeolite (pore size: about 7 Å).

The FER type zeolite is represented by the following general formula when it is on an anhydrous basis:

$$0.5\sim1.5M_{2/n}\cdot Y_2O_3\cdot xSiO_2$$

wherein M denotes an n-valent cation; Y is one or more element(s) selected from the group consisting of Al, Fe, Cr, V, Mo, As, Mn, Ga and B; and x is 10–200, preferably 12–100.

It is advantageous that the primary-particle size of crystals of said zeolite is small. When the volumes of particles of the crystals are converted to those of spherical particles, the average diameter of the spherical particles is preferably 2 μm or less, more preferably 0.5 μm or less.

Although the FER type zeolite used in the present invention can be used after being washed, dried and then calcined in an inert gas atmosphere of air, nitrogen or the like after its synthesis, it is preferably used after being converted to Ag form, polyvalent-metal-cation type or H form (proton form), preferably to H form, by ion exchange. A method for the conversion to H form by ion exchange is hot particularly limited. A known method, such as a method wherein the FER type zeolite is subjected to ion exchange in an aqueous ammonium salt solution and then calcination to convert the same to H form, and a method comprising ion-exchange of the FER type zeolite in an aqueous mineral acid solution. When the ion exchange is carried out in the aqueous mineral acid solution, the acid used is preferably nitric acid or hydrochloric acid, most preferably nitric acid. Preferable ion exchange conditions are as follows: said zeolite is dispersed in an aqueous mineral acid solution with a normality of 0.1–2 so that the concentration of the resulting slurry of said zeolite would be 2 to 30%, and the slurry is stirred at a room temperature or at 100° C. or lower for several hours to convert the zeolite to proton form by ion exchange. After the conversion to proton form, the thus treated zeolite is filtered, washed and then dried.

Specific examples of the oxide or compound oxide (excluding crystalline aluminosilicate zeolites) used in the present invention, which comprises one or more elements selected from the group consisting of elements belonging to group 4 (group IVA), group 13 (group IIIB) and group 14 (group IVB) of the periodic table, include alumina, titanium oxide, indium oxide, silica, and silica-alumina. Of these, alumina is preferred and γ-alumina is especially preferred.

The surface area of the above-mentioned oxide or compound oxide used in the present invention is preferably large. Specifically, the surface area is 20 m²/g or more, preferably 100 m²/g or more, more preferably 150 m²/g or more.

The above-mentioned oxide or compound oxide used in the present invention is preferably used after being brought into contact with one or more acid(s) selected from sulfuric acid and monobasic acids, and then washed with water until the washings become free from the acid(s). Specifically, the sulfuric acid and monobasic acids are sulfuric acid and monobasic inorganic and organic acids, and are preferably sulfuric acid, nitric acid, hydrochloric acid and acetic acid, more preferably nitric acid and sulfuric acid. As to a method for bringing the aforesaid oxide or compound oxide into contact with the acid(s), the aforesaid oxide or compound oxide may be treated either as it is or after being shaped. The contact can be made, for example, by dispersing a catalyst containing the aforesaid oxide or compound oxide in an aqueous solution of the aforesaid acid(s), or by passing an aqueous solution of the acid(s) through a packed bed of said catalyst. In this case, the concentration of the aqueous solution of the acid(s) should be determined depending on the acid resistance of the catalyst, though it is generally 0.002–2 normal, preferably 0.01–0.5 normal, more preferably 0.05–0.2 normal. The treatment temperature is 100° C. or lower, preferably 0–60° C., more preferably 20–40° C. The treatment time is 0.01–1000 hours, preferably 0.1–100 hours. Then, the thus treated oxide or compound oxide is thoroughly washed with water until the washings become free from the acid(s). The term "thorough washing" means washing with pure water in an amount of 5 times or more, preferably 20 times or more, more preferably 50 times or more, the mass of the catalyst. For confirming the thorough washing, it is preferable to further wash the washed oxide or compound oxide with pure water in the same amount as above until the pH of the washings does not increase by 0.2 or more, preferably 0.1 or more, as compared with that of the washings obtained in the previous washing operation.

As the water used for the washing after the contact with the acid(s), pure water freed from impurities, metal ions and the like by any of filtration, distillation, reverse osmosis and ion exchange or by a combination thereof and having a resistivity of 5 MΩ·cm or more is, preferably used.

The catalyst used in the production process of the present invention must have a pH of 6 or less at 20° C., when made into a slurry by dispersing said catalyst in a quantity of water 5 times as much as the quantity of catalyst by weight ratio. When the pH is higher than 6, the activity of the catalyst is undesirably lowered. Although the lower limit of the pH is not particularly limited, the pH is normally 3 or more. When the pH is 3 to 6, a high selectivity of 3-hydroxypropanal in the hydration of acrolein can be attained, which is a feature of the present invention. For confirming that the pH is 6 or less at 20° C., when made into a slurry by dispersing the catalyst in a quantity of water 5 times as much as the quantity of catalyst by weight ratio, is 6 or lower, it is made sure that there is no residual acid, alkali or the like, which has adhered to the catalyst during the synthesis and the ion exchange, in the catalyst by previously washing the catalyst with pure water thoroughly to make sure that the pH of the pure water after the washing is in a ±0.3 range of the pH of the pure water before the washing. As the pure water used in this case, pure water freed from impurities, metal ions and the like by any of filtration, distillation, reverse osmosis and ion exchange or by a combination thereof and having a resistivity of 5 MΩ·cm or more is preferably used. The pH of the slurry is measured while stirring the slurry thoroughly. When the pH of the slurry is measured at a temperature other than 20° C., the pH at 20° C. may be obtained by converting the measured value.

As the catalyst used in the production process of the present invention, although each of the metalloaluminophosphate molecular sieve, the FER type zeolite, and the oxide or compound oxide comprising one or more elements selected from elements belonging to group 4, group 13 and group 14 of the periodic table may be used alone, a catalyst obtained by combining the metalloaluminophosphate molecular sieve and/or the FER type zeolite and the oxide or compound oxide comprising one or more elements selected from elements belonging to group 4, group 13 and group 14 of the periodic table is also preferred. Preferable specific examples of the catalyst are combinations of SAPO-34 and/or SAPO-11 and/or ferrierite/alumina, in particular, a combination of SAPO-34/alumina and a combination of ferrierite/alumina.

The catalyst used in the present invention can be used in powder form or after being molded, depending on the reactor type. For the shaping, graphite, carbon black or the like may be added as a molding auxiliary substance.

When the catalytic activity of the catalyst used in the present invention is lowered after its long-term use in the hydration reaction, it can be regenerated by calcining at a temperature of 300–700° C., preferably 350–600° C., more preferably 400–550° C., in an air atmosphere or an air/inert gas (e.g. nitrogen, carbon dioxide or argon) atmosphere. Owing to this regenerating treatment, the catalyst regains its initial activity and hence can be re-used as the above-mentioned hydration reaction catalyst. This is an advantage of said catalyst which an ion-exchange resin catalyst cannot have.

As the hydration reaction conditions in the present invention, the reaction temperature is 20–200° C., preferably 30–120° C., more preferably 40–80° C., and the reaction pressure is 0.1–10 MPa, preferably 0.1–2 MPa, more preferably 0.1–1 MPa. The weight ratio of the starting acrolein to water is 1:2–1:20, preferably 1:3–1:20, more preferably 1:4–1:10. When the reaction temperature is raised, the reaction rate is increased but side reactions due to heat are more remarkably increased. Therefore, the reaction is preferably carried out at as a low temperature as possible. The reaction pressure is not particularly limited so long as it is sufficient to keep the reaction system in a liquid phase. Although the reaction can be carried out under a reduced pressure, it is usually carried out at atmospheric pressure or under pressure. When water is added to the starting acrolein in an amount of more than 20 times the weight of the staring acrolein, the productivity is undesirably decreased. When water is added to the starting acrolein in an amount of less than 2 times the weight of the staring acrolein, the selectivity of 3-hydroxypropanal, i.e., the desired product is undesirably decreased. When the weight ratio of acrolein to water is set at 1:3–1:20, preferably 1:4–1:10, acrolein is dissolved in water, so that it can be supplied to a reaction system in the form of an aqueous acrolein solution, which is preferred.

A polymerization retarder such as hydroquinone, hydroquinone monomethyl ether or the like may be added to the reaction system so long as it is effective in retarding the polymerization of acrolein but not the hydration reaction of iterest.

In the present invention, although the hydration reaction can be carried out in either a batch-type reactor or a continuous reactor, it is preferably carried out in the continuous reactor. The type of the reactor is also not particularly limited, but a stirring tank type reactor, a loop type reactor, a hanging-bed type reactor, a fluidized-bed reactor, a packed-bed type fixed-bed reactor, a multi-tubular fixed-bed reactor and the like can be used. When the reaction is carried out in the continuous reactor, the material feed rate is preferably controlled so that the one-pass conversion rate of the starting acrolein may be 20 to 95%, preferably 30 to 80%, more preferably 40 to 70%. In this case, WHSV is operated at usually 0.1 to 20 hr$^{-1}$, preferably 0.2 to 3 hr$^{-1}$.

In the production process of the present invention, if any unreacted acrolein is present after the hydration reaction of acrolein, any unreacted acrolein is separated from the reaction product. If the catalyst separation from the reaction product is necessary, the unreacted acrolein is separated after the catalyst is separated from the reaction product by precipitation or filtration. The unreacted acrolein can be separated preferably by distillation, in particular, distillation under reduced pressure at a temperature of 80° C. or lower. An acrolein-free aqueous solution of 3-hydroxypropanal (3-HPA) obtained by separating the unreacted acrolein by distillation can be concentrated by the use of, for example, a thin-layer evaporator before the hydrogenation. The separated water and unreacted acrolein can be recycled to the hydration reaction system. The separated catalyst can also be repeatedly used in the hydration reaction. When the hydration reaction of acrolein is carried out in a fixed-bed reactor, the above-mentioned separation of the catalyst is not required, which is thus preferred.

In the 3-HPA aqueous solution, 3-HPA can be converted to 1,3-propanediol by hydrogenating treatment in a liquid or gas phase at 30 to 200° C. and a hydrogen pressure of 0.1 to 20 MPa in a conventional hydrogenation reactor in the presence of a hydrogenation catalyst such as Raney nickel, other nickel-based catalysts, palladium-based catalyst, platinum-based catalyst, ruthenium-based catalyst or the like. Especially preferably, the hydrogenation can be carried out in a liquid phase at 40–120° C. and a hydrogen pressure of 1–15 MPa by using Raney nickel (into which any of various other metals may be doped), supported nickel, palladium, platinum or ruthenium as a catalyst.

1,3-Propanediol can be recovered by separating water and by-products from the hydrogenation product, for example, by well-known distillation.

The present invention is described in detail by way of the following examples and comparative examples.

EXAMPLE 1

SAPO-34 was prepared according to EXAMPLE 33 in the specification of U.S. Pat. No. 4,440,871. Pure water 146.7 g and 95.9 g of a 85% by weight aqueous $H_3PO_4$ solution were mixed and. 169.6 g of aluminum isopropoxide ($Al(OC_3H_7)_3$) was added thereto, and stirred. To the resulting mixture was added 2.6 g of silica powder, and stirred until it became homogeneous. Subsequently, 305.2 g of a 20% by weight aqueous tetraethylammonium hydroxide (($C_2H_5)_4$NOH) solution was added thereto and the resulting mixture was stirred until it became homogeneous. The stirred mixture was subjected to hydrothermal synthesis in a 1-L autoclave at 150° C. for 133 hours.

After the hydrothermal synthesis, the synthesis product was filtered, washed and then dried, and the resulting crystal powder was calcined in air at 500° C. for 2 hours. A portion of the crystal powder was analyzed by a powder X-ray diffraction method (a powder diffraction X-ray measuring apparatus RAD-IIIA, mfd. by RIGAKU CORPORATION) to be confirmed as SAPO-34. In addition, the crystal powder was analyzed with an energy dispersion type X-ray analyzer (EMAX-5770W, mfd. by HORIBA LTD.) connected to a scanning electron microscope (X650, mfd. by HITACHI LTD.) to find that the molar ratio of $(P_2O_5+Al_2O_3)/SiO_2$ was 10.

The calcined crystal powder was added to a 1N aqueous $NH_4NO_3$ solution to obtain a 10% by weight slurry, and the slurry was subjected to ion exchange at a room temperature for 3 hours, filtered and washed with pure water, dried at 120° C. for 10 hours, and then calcined at 530° C. for 3 hours to obtain H form SAPO-34 (catalyst A).

Ten grams of catalyst A and 50 g of pure water were introduced into a 100-ml glass beaker, and the pH of the resulting slurry was measured while stirring the slurry by the use of a rotator, a fluororesin-coated magnet, with a diameter of 5 mm and a length of 25 mm to find that the pH at 20° C. was 4.3. For this pH measurement, a glass electrode type hydrogen ion concentration meter (pH METER M-8AD) manufactured by HORIBA LTD. was used.

After 10 g of catalyst A and 30 g of pure water were introduced into a 50-ml heat-resistant glass bottle, a rotator, a fluororesin-coated magnet, with a diameter of 5 mm and a length of 25 mm was placed therein. Then, 7 g of acrolein (mfd. by Tokyo Kasei Co., Ltd.) was added thereto, and the cap of the heat-resistant glass bottle was placed. The heat-resistant glass bottle was soaked in a hot water bath on a magnetic stirrer equipped with a heater, and was maintained at 60° C. for 4 hours while rotating the rotator in the heat-resistant glass bottle. Thereafter, the heat-resistant glass bottle was soaked in cold water at 0° C. to cool its contents to 5° C. or lower, and the contents of the heat-resistant glass bottle were filtered. Acetone was added to the filtrate as an internal standard in an amount of 5% and they were thoroughly mixed, followed by analysis by gas chromatography. The analysis conditions were as follows:

apparatus: Shimadzu Model GC-17A,
column: SPB-1 mfd. by S & W Co., Ltd.; L 60 m×ID 0.25 mm×membrane thickness 3 μm,
carrier gas: nitrogen, column flow rate 1 ml/min, split ratio 100,
heating program: maintenance at 70° C. for 10 minutes, followed by heating up to 250° C. at a rate of 5° C./min. and maintenance at 250° C. for 30 minutes.

The reaction results are shown in Table 3. The conversion rate of acrolein was 49% and the selectivity of 3-hydroxypropionaldehyde (3-HPA) was 96 mol %.

EXAMPLE 2

Hydration reaction of acrolein using catalyst A was carried out under the same conditions as in Example 1 except for changing the reaction time to 8 hours. The reaction results are as shown in Table 3, namely, the conversion rate of acrolein was 72% and the selectivity of 3-hydroxypropionaldehyde (3-HPA) was 94 mol %. It can be seen that when catalyst A is used, the selectivity of 3-hydroxypropionaldehyde (3-HPA) is kept high even under conditions under which the conversion rate of acrolein is high.

EXAMPLE 3

SAPO-11 was prepared according to EXAMPLE 15 in the specification of U.S. Pat. No. 4,440,871. Pure water 353.8 g and 113.4 g of a 85% by weight aqueous $H_3PO_4$ solution were mixed, 200.6 g of aluminum isopropoxide ($Al(OC_3H_7)_3$) was added thereto and stirred. To the resulting mixture was added 3.1 g of silica powder, and the mixture thus obtained was stirred until it became homogeneous. Subsequently, 49.1 g of di-n-propylamine (($C_3H_7)_2NH$) was added thereto and the resulting mixture was stirred until it became homogeneous. The stirred mixture was subjected to hydrothermal synthesis in a 1-L autoclave at 150° C. for 133 hours.

After the hydrothermal synthesis, the synthesis product was filtered, washed and then dried, and the resulting crystal powder was calcined in air at 500° C. for 2 hours. A portion of the crystal powder was analyzed by a powder X-ray diffraction method (a powder diffraction X-ray measuring apparatus RAD-IIIA, mfd. by RIGAKU CORPORATION) to be confirmed as SAPO-11. In addition, the crystal powder was analyzed with an energy dispersion type X-ray analyzer (EMAX-5770W, mfd. by HORIBA LTD.) connected to a scanning electron microscope (X650, mfd. by HITACHI LTD.) to find that the molar ratio of $(P_2O_5+Al_2O_3)/SiO_2$ was 10.

The calcined crystal powder was added to a 1N aqueous $NH_4NO_3$ solution to obtain a 10% by weight slurry, and the slurry was subjected to ion exchange at room temperature for 3 hours. After filtration, the precipitate was washed with pure water, dried at 120° C. for 10 hours, and then calcined at 530° C. for 3 hours to obtain H form SAPO-11 (catalyst B).

Ten grams of catalyst B and 50 g of pure water were placed in a 100-ml glass beaker, and the pH of the resulting slurry was measured while stirring the slurry by the use of a rotator, a fluororesin-coated magnet, with a diameter of 5 mm and a length of 25 mm to find that the pH at 20° C. was 5.6. For this pH measurement, a glass electrode type hydrogen ion concentration meter (pH METER M-8AD) manufactured by HORIBA LTD. was used.

Hydration reaction of acrolein was carried out under the same conditions as in Example 2 except for using catalyst B. The reaction results are shown in Table 3. The conversion rate of acrolein was 50% and the selectivity of 3-hydroxypropionaldehyde (3-HPA) was 88 mol %.

EXAMPLE 4

Ferrierite (HSZ-720KOA; $SiO_2/Al_2O_3$ molar ratio 18) manufactured by TOSOH CORPORATION was calcined at 530° C. for 3 hours in an air atmosphere. Fifty grams of calcined ferrierite was dispersed in 450 g of a 1N aqueous $HNO_3$ solution, and the resulting dispersion was stirred at room temperature for 2 hours, thoroughly washed with pure water, and then dried at 120° C. for 5 hours to obtain catalyst C.

Ten grams of catalyst C and 50 g of pure water were introduced into a 100-ml glass beaker, and the pH of the resulting slurry was measured while stirring the slurry by the use of a rotator, a fluororesin-coated magnet, with a diameter of 5 mm and a length of 25 mm to find that the pH at 20° C. was 3.1. For this pH measurement, a glass electrode type hydrogen ion concentration meter (pH METER M-8AD) manufactured by HORIBA LTD. was used.

Hydration reaction of acrolein using catalyst A was carried out under the same conditions as in Example 1 except that the reaction time was changed to 5 hours. The results thereof are shown in Table 3. The conversion rate of acrolein was 77% and the selectivity of 3-hydroxypropionaldehyde (3-HPA) was 88 mol %.

COMPARATIVE EXAMPLE 1

Hydration reaction of acrolein was carried out under the same conditions as in Example 1 except that 15 g of H form ZSM-5 (CBV3024E; $SiO_2/Al_2O_3$=30; manufactured by ZEOLYST Corp., $NH_4$ form ZSM-5 was calcined at 530° C. for 3 hours in an air atmosphere) was used and that the reaction time was changed to 1 hour. The results are shown in Table 3. The conversion rate of acrolein was 87% and the selectivity of 3-hydroxypropionaldehyde (3-HPA) was 51 mol %.

COMPARATIVE EXAMPLE 2

Hydration reaction of acrolein using the H form ZSM-5 catalyst was carried out under the same conditions as in Comparative Example 1 except that the reaction temperature was changed to 40° C. and that the reaction time was changed to 2 hours. The results are shown in Table 3. The conversion rate of acrolein was 64% and the selectivity of 3-hydroxypropionaldehyde (3-HPA) was 54 mol %.

TABLE 3

| Example | Catalyst | Reaction conditions | | | | | Conversion rate of acrolein (%) | Selectivity of 3-HPA (mol %) |
|---|---|---|---|---|---|---|---|---|
| | | Temperature (° C.) | Reaction time (Hr) | Amount of catalyst (g) | Amount of acrolein (g) | Amount of water (g) | | |
| Example 1 | SAPO-34 | 60 | 4 | 10 | 7 | 30 | 49 | 96 |
| Example 2 | SAPO-34 | 60 | 8 | 10 | 7 | 30 | 72 | 94 |
| Example 3 | SAPO-11 | 60 | 8 | 10 | 7 | 30 | 50 | 88 |
| Example 4 | Ferrierite | 60 | 5 | 10 | 7 | 30 | 77 | 88 |
| Comparative Example 1 | ZSM-5 | 60 | 1 | 15 | 7 | 30 | 87 | 51 |
| Comparative Example 2 | ZSM-5 | 40 | 2 | 15 | 7 | 30 | 64 | 54 |

EXAMPLE 5

Fifty grams of high-purity γ alumina NRK301 ($Al_2O_3$ purity 99.9% by weight, and surface area 282 $m^2/g$) manufactured by Nishio Kogyo Co., Ltd. was dispersed in 450 g of a 0.1N aqueous $HNO_3$ solution, and the resulting dispersion was stirred at a room temperature for 2 hours and filtered, after which the residue was washed with 3 L of pure water and then dried at 120° C. for 5 hours to obtain catalyst D.

Ten grams of catalyst D and 50 g of pure water were introduced into a 100-ml glass beaker, and the pH of the resulting slurry was measured while stirring the slurry by the use of a rotator, a fluororesin-coated magnet, with a diameter of 5 mm and a length of 25 mm to find that the pH at 20° C. was 3.7. For this pH measurement, a glass electrode type hydrogen ion concentration meter (pH METER M-8AD) manufactured by HORIBA LTD. was used.

Hydration reaction of acrolein using catalyst D was carried out under the same conditions as in Example 1 except that the reaction time was changed to 2 hours. The results are shown in Table 4. The conversion rate of acrolein was 58% and the selectivity of 3-hydroxypropionaldehyde (3-HPA) was 89 mol %.

EXAMPLE 6

Fifty grams of high-purity γ alumina NRK401 ($Al_2O_3$ purity 99.99% by weight, and surface area 282 $m^2/g$) manufactured by Nishio Kogyo Co., Ltd. was dispersed in 450 g of a 0.1N aqueous $HNO_3$ solution, and the resulting dispersion was stirred at a room temperature for 2 hours and filtered, after which the residue was washed with 3 L of pure water and then dried at 120° C. for 5 hours to obtain catalyst E. Ten grams of catalyst E and 50 g of pure water were introduced into a 100-ml glass beaker, and the pH of the resulting slurry was measured while stirring the slurry by the use of a rotator, a fluororesin-coated magnet, with a diameter of 5 mm and a length of 25 mm to find that the pH at 20° C. was 3.6. For this pH measurement, a glass electrode type hydrogen ion concentration meter (pH METER M-8AD) manufactured by HORIBA LTD. was used.

Hydration reaction of acrolein was carried out under the same conditions as in Example 5 except that the catalyst was changed to catalyst E. The results are shown in Table 4. The conversion rate of acrolein was 54% and the selectivity of 3-hydroxypropionaldehyde (3-HPA) was 90 mol %.

EXAMPLE 7

Fifty grams of an alumina catalyst N613CP ($Al_2O_3$ purity 99.8% by weight, and surface area 168 $m^2/g$) manufactured by Nikki Chemical Co., Ltd. was dispersed in 450 g of a 0.5N aqueous $HNO_3$ solution, and the resulting dispersion was stirred at a room temperature for 2 hours and filtered, after which the residue was washed with 3 L of pure water and then dried at 120° C. for 5 hours to obtain catalyst F. Ten grams of catalyst F and 50 g of pure water were placed in a 100-ml glass beaker, and the pH of the resulting slurry was measured while stirring the slurry by the use of a rotator, a fluororesin-coated magnet, with a diameter of 5 mm and a length of 25 mm to find that the pH at 20° C. was 3.7. For this pH measurement, a glass electrode type hydrogen ion concentration meter (pH METER M-8AD) manufactured by HORIBA LTD. was used. Hydration reaction of acrolein was carried out under the same conditions as in Example 5 except that the catalyst was changed to catalyst F. The results are shown in Table 4. The conversion rate of acrolein was 57% and the selectivity of 3-hydroxypropionaldehyde (3-HPA) was 88 mol %.

EXAMPLE 8

Fifty grams of γ alumina AC-12 ($Al_2O_3$ purity 99.7% by weight, and surface area 120 $m^2/g$) manufactured by Nishio Kogyo Co., Ltd. was dispersed in 450 g of a 0.1N aqueous $HNO_3$ solution, and the resulting dispersion was stirred at a room temperature for 2 hours and filtered, after which the residue was washed with 3 L of pure water and then dried at 120° C. for 5 hours to obtain catalyst G. Ten grams of catalyst G and 50 g of pure water were placed in a 100-ml glass beaker, and the pH of the resulting slurry was measured while stirring the slurry by the use of a rotator, a fluororesin-coated magnet, with a diameter of 5 mm and a length of 25 mm to find that the pH at 20° C. was 4.4. For this pH measurement, a glass electrode type hydrogen ion concentration meter (pH METER M-8AD) manufactured by HORIBA LTD. was used.

Hydration reaction of acrolein was carried out under the same conditions as in Example 5 except that the catalyst was changed to catalyst G and that the amount of the catalyst was changed to 16 g. The results are shown in Table 4. The conversion rate of acrolein was 45% and the selectivity of 3-hydroxypropionaldehyde (3-HPA) was 90 mol %.

EXAMPLE 9

Fifty grams of high-purity γ alumina NRK301 ($Al_2O_3$ purity 99.9% by weight, and surface area 282 $m^2/g$) manufactured by Nishio Kogyo Co., Ltd. was dispersed in 450 g of a 0.01N aqueous $HNO_3$ solution, and the resulting dispersion was stirred at room temperature for 2 hours and filtered, after which the residue was washed with 3 L of pure water and then dried at 120° C. for 5 hours to obtain catalyst H.

Ten grams of catalyst H and 50 g of pure water were placed in a 100-ml glass beaker, and the pH of the resulting slurry was measured while stirring the slurry by the use of a rotator, a fluororesin-coated magnet, with a diameter of 5 mm and a length of 25 mm to find that the pH at 20° C. was 3.9. For this pH measurement, a glass electrode type hydrogen ion concentration meter (pH METER M-8AD) manufactured by HORIBA LTD. was used.

Hydration reaction of acrolein was carried out under the same conditions as in Example 5 except that the catalyst was changed to catalyst H. The results are shown in Table 4. The conversion of acrolein was 57% and the selectivity of 3-hydroxypropionaldehyde (3-HPA) was 89 mol %.

COMPARATIVE EXAMPLE 3

The same high-purity γ alumina (NRK301, mfd. by Nishio Kogyo Co., Ltd.) as used in Examples 5 and 9 was used as it was as comparative catalyst B. Ten grams of comparative catalyst B and 50 g of pure water were introduced in a 100-ml glass beaker, and the pH of the resulting slurry was measured while stirring the slurry by the use of a rotator, a fluororesin-coated magnet, with a diameter of 5 mm and a length of 25 mm to find that the pH at 20° C. was 6.7. For this pH measurement, a glass electrode type hydrogen ion concentration meter (pH METER M-8AD) manufactured by HORIBA LTD. was used.

Hydration reaction of acrolein was carried out under the same conditions as in Example 5 except that the catalyst was changed to comparative catalyst B. The results are shown in Table 4. The conversion rate of acrolein was 69% and the selectivity of 3-hydroxypropionaldehyde (3-HPA) was 73 mol %.

COMPARATIVE EXAMPLE 4

Fifty grams of the same high-purity γ alumina NRK301 (mfd. by Nishio Kogyo Co., Ltd.; $Al_2O_3$ purity 99.9% by weight, and surface area 282 $m^2/g$) as used in Examples 5 and 9 was dispersed in 450 g of a 0.001N aqueous $HNO_3$ solution, and the resulting dispersion was stirred at a room temperature for 2 hours and filtered, after which the residue was washed with 3 L of pure water and then dried at 120° C. for 5 hours to obtain comparative catalyst C.

Ten grams of comparative catalyst C and 50 g of pure water were introduced into a 100-ml glass beaker, and the pH of the resulting slurry was measured while stirring the slurry by the use of a rotator, a fluororesin-coated magnet, with a diameter of 5 mm and a length of 25 mm to find that the pH at 20° C. was 6.1. For this pH measurement, a glass electrode type hydrogen ion concentration meter (pH METER M-8AD) manufactured by HORIBA LTD. was used.

Hydration reaction of acrolein was carried out under the same conditions as in Example 2 except that the catalyst was changed to comparative catalyst C. The results are shown in Table 4. The conversion rate of acrolein was 64% and the selectivity of 3-hydroxypropionaldehyde (3-HPA) was 76 mol %.

TABLE 4

| | | | Reaction conditions | | | |
| --- | --- | --- | --- | --- | --- | --- |
| Example | Catalyst | pH of aqueous slurry | Temperature (° C.) | Reaction time (Hr) | Amount of catalyst (g) | Conversion rate of acrolein (%) | Selectivity of 3-HPA (mol %) |
| Example 5 | Catalyst D | 3.7 | 60 | 2 | 10 | 58 | 89 |
| Example 6 | Catalyst E | 3.6 | 60 | 2 | 10 | 54 | 90 |
| Example 7 | Catalyst F | 3.7 | 60 | 2 | 10 | 57 | 88 |
| Example 8 | Catalyst G | 4.4 | 60 | 2 | 16 | 45 | 90 |
| Example 9 | Catalyst H | 3.9 | 60 | 2 | 10 | 57 | 89 |
| Comparative Example 3 | Comparative Catalyst B | 6.7 | 60 | 2 | 10 | 69 | 73 |
| Comparative Example 4 | Comparative Catalyst C | 6.1 | 60 | 2 | 10 | 64 | 76 |

EXAMPLE 10

Fifty grams of indium oxide ($In_2O_3$, 99.9% by weight) manufactured by Wako Pure Chemical Industries, Ltd. was dispersed in 450 g of a 0.1N aqueous $HNO_3$ solution, and the resulting dispersion was stirred at a room temperature for 2 hours and filtered, after which the residue was washed with 3 L of pure water and then dried at 120° C. for 5 hours to obtain catalyst I. Ten grams of catalyst I and 50 g of pure water were introduced into a 100-ml glass beaker, and the pH of the resulting slurry was measured while stirring the slurry by the use of a rotator, a fluororesin-coated magnet, with a diameter of 5 mm and a length of 25 mm to find that the pH at 20° C. was 3.0. For this pH measurement, a glass electrode type hydrogen ion concentration meter (pH METER M-8AD) manufactured by HORIBA LTD. was used. Hydration reaction of acrolein was carried out under the same conditions as in Example 5 except that the catalyst was changed to catalyst I. The results are shown in Table 5. The conversion rate of acrolein was 36% and the selectivity of 3-hydroxypropionaldehyde (3-HPA) was 93 mol %.

EXAMPLE 11

Fifty grams of titanium dioxide (anatase type) manufactured by Wako Pure Chemical Industries, Ltd. was dispersed in 450 g of a 0.1N aqueous $HNO_3$ solution, and the resulting dispersion was stirred at room temperature for 2 hours and filtered, after which the residue was washed with 3 L of pure water and then dried at 120° C. for 5 hours to obtain catalyst J. Ten grams of catalyst J and 50 g of pure water were introduced into a 100-ml glass beaker, and the pH of the resulting slurry was measured while stirring the slurry by the use of a rotator, a TEFLON®-coated magnet, with a diameter of 5 mm and a length of 25 mm to find that the pH at 20° C. was 3.8. For this pH measurement, a glass electrode type hydrogen ion concentration meter (pH METER M-8AD) manufactured by HORIBA LTD. was used. Hydration reaction of acrolein was carried out under the same conditions as in Example 5 except that the catalyst was changed to catalyst J. The results are shown in Table 5. The conversion rate of acrolein was 18% and the selectivity of 3-hydroxypropionaldehyde (3-HPA) was 95 mol %.

EXAMPLE 12

Two hundred grams of tetraethyl orthosilicate (95% by weight) manufactured by Wako Pure Chemical Industries, Ltd. was placed in an evaporating dish, dried at 120° C. for 20 hrs, and then calcined in an electric furnace at 500° C. for 3 hrs in an air atmosphere to produce $SiO_2$. This $SiO_2$ was used as catalyst K. Ten grams of catalyst K and 50 g of pure water were introduced into a 100-ml glass beaker, and the pH of the resulting slurry was measured while stirring the slurry by the use of a rotator, a fluororesin-coated magnet, with a diameter of 5 mm and a length of 25 mm to find that the pH at 20° C. was 3.6. For this pH measurement, a glass electrode type hydrogen ion concentration meter (pH METER M-8AD) manufactured by HORIBA LTD. was used. Hydration reaction of acrolein was carried out under the same conditions as in Example 5 except that the catalyst was changed to catalyst K, the amount of the catalyst to 16 g, and the reaction time to 5 hours. The results are shown in Table 5. The conversion rate of acrolein was 20% and the selectivity of 3-hydroxypropionaldehyde (3-HPA) was 94 mol %.

COMPARATIVE EXAMPLE 5

Fifty grams of titanium dioxide (anatase type) manufactured by Wako Pure Chemical Industries, Ltd. was added to 65 g of a 20% aqueous phosphoric acid solution and stirred, and the resulting mixture was allowed to stand for 12 hrs, dried at 150° C. for 4 hrs, calcined at 450° C. for 1 hr in an air atmosphere, cooled, and then ground to 200-mesh to obtain comparative catalyst D. Ten grams of comparatice catalyst D and 50 g of pure water were introduced into a 100-ml glass beaker, and the pH of the resulting slurry was measured while stirring the slurry by the use of a rotator, a fluororesin coated magnet, with a diameter of 5 mm and a length of 25 mm to find that the pH at 20° C. was 2.7. For this pH measurement, a glass electrode type hydrogen ion concentration meter (pH METER M-8AD) manufactured by HORIBA LTD. was used.

Hydration reaction of acrolein was carried out under the same conditions as in Example 5 except that the catalyst was changed to comparatice catalyst D. The results are shown in Table 5. The conversion rate of acrolein was 13% and the selectivity of 3-hydroxypropionaldehyde (3-HPA) was 86 mol %. Thus, when the catalyst supporting phosphoric acid was used which is not included in the present invention, the selectivity of 3-hydroxypropionaldehyde (3-HPA) was lowered as can be seen by comparison with the result obtained in Example 11.

EXAMPLE 13

Two hundred grams of H form SAPO-34 prepared in the same manner as in Example 1 and 500 g of Alumina Sol-200 manufactured by Nissan Chemical Industries Ltd. were mixed and then extrusion-molded to obtain a molded product (SAPO-34/alumina=80/20) with a diameter of about 1.6 mm and a length of approximately 3 to 5 mm. The molded product was dried at 120° C. for 5 hours and then calcined at 530° C. for 3 hours in an air atmosphere. Hundred grams of the calcined molded product was dispersed in 900 g of a 0.01N aqueous $HNO_3$ solution, and the resulting dispersion was stirred at room temperature for 2 hours, thoroughly washed with pure water, and then dried at 120° C. for 5 hours to obtain catalyst L.

Catalyst L was crushed in a mortar, and 10 g of the resulting powder and 50 g of pure water were introduced into a 100-ml glass beaker, and the pH of the resulting slurry was measured while stirring the slurry by the use of a rotator, a fluororesin coated magnet, with a diameter of 5 mm and a length of 25 mm to find that the pH at 20° C. was 4.5. For this pH measurement, a glass electrode type hydrogen ion concentration meter (pH METER M-8AD) manufactured by HORIBA LTD. was used.

After 10 g of catalyst L and 30 g of pure water were introduced into a 50-ml heat-resistant glass bottle, a rotator, a fluororesin coated magnet, with a diameter of 5 mm and a length of 25 mm was placed therein. Then, 7.5 g of acrolein (mfd. by Tokyo Kasei Co., Ltd.) was added thereto, and the cap the heat-resistant glass bottle was placed. The heat-resistant glass bottle was soaked in a hot water bath on a magnetic stirrer equipped with a heater, and was maintained at 60° C. for 4 hours while rotating the rotator in the heat-resistant glass bottle. Thereafter, the heat-resistant glass bottle was soaked in cold water at 0° C. to cool its contents to 5° C. or lower, and the contents of the heat-resistant glass bottle were filtered. Acetone was added to the filtrate as an internal standard in an amount of 5% and it was thoroughly mixed, followed by analysis by gas chromatography.

The reaction results are shown in Table 6. The conversion rate of acrolein was 62% and the selectivity of 3-hydroxypropionaldehyde (3-HPA) was 92 mol %.

EXAMPLE 14

Fifty grams of a ferrierite/alumina extrusion-molded product (CP914B-20CY; alumina 20% by weight, and $SiO_2$/$Al_2O_3$ ratio of ferrierite: 20) manufactured by ZEOLYST Corp. was dispersed in 450 g of a 0.5N aqueous $HNO_3$ solution, and the resulting dispersion was stirred at a room temperature for 2 hours, thoroughly washed with pure water, and then dried at 120° C. for 5 hours to obtain catalyst M.

Catalyst M was crushed in a mortar, and 10 g of the resulting powder and 50 g of pure water were introduced

TABLE 5

| | | | Reaction conditions | | | |
| --- | --- | --- | --- | --- | --- | --- |
| Example | Catalyst | pH of 10% aqueous slurry | Temperature (° C.) | Reaction time (Hr) | Amount of catalyst (g) | Conversion rate of acrolein (%) | Selectivity of 3-HPA (mol %) |
| Example 10 | Catalyst I | 3.0 | 60 | 2 | 10 | 36 | 93 |
| Example 11 | Catalyst J | 3.8 | 60 | 2 | 10 | 18 | 95 |
| Example 12 | Catalyst K | 3.6 | 60 | 5 | 6 | 20 | 94 |
| Comparative Example 5 | Comparative Catalyst D | 2.7 | 60 | 2 | 10 | 13 | 86 | into a 100-ml glass beaker, and the pH of the resulting slurry was measured while stirring the slurry by the use of a rotator, a fluororesin-coated magnet, with a diameter of 5 mm and a length of 25 mm to find that the pH at 20° C. was 4.4. For this pH measurement, a glass electrode type hydrogen ion concentration meter (pH METER M-8AD) manufactured by HORIBA LTD. was used.

Hydration reaction of acrolein using catalyst M was carried out under the same conditions as in Example 13 except that catalyst M was used. The results are shown in Table 6. The conversion rate of acrolein was 71% and the selectivity of 3-hydroxypropionaldehyde (3-HPA) was 88 mol %.

COMPARATIVE EXAMPLE 6

An ion-exchange resin Lewatit (trademark) TP208 (functional group: iminodiacetic acid) manufactured by Bayer AG, the same ion-exchange resin as used in the example of European Patent Application Laid-Open No. 0487903, was immersed in a 1N aqueous hydrochloric acid solution 10 time as much as the ion-exchange resin by volume, and stirred for 1 hour. After decantation, the thus treated ion-exchange resin was washed ten times with pure water 10 times as much as the ion-exchange resin by volume to be converted to H form.

Hydration reaction of acrolein was carried out under the same conditions as in Example 13 except that 13.8 ml of the H type Lewatit (trade name) TP208 was used and the reaction time was changed to 45 minutes. The results are shown in Table 6. The conversion rate of acrolein was 60% and the selectivity of 3-hydroxypropionaldehyde (3-HPA) was 79 mol %.

EXAMPLE 16

The hydration reaction product obtained in Example 15 was subjected to simple distillation at 60° C. under a reduced pressure of 100 Torr to distill out the unreacted acrolein completely, whereby an approx. 11% by weight aqueous 3-hydroxypropionaldehyde solution was obtained. Thirty grams of the aqueous 3-hydroxypropionaldehyde solution and 0.3 g of a Raney nickel catalyst (NDHT-90, containing 5.3% Al) manufactured by Kawaken Fine Chemicals Co., Ltd. were charged into a 200-ml autoclave, and hydrogenation reaction was carried out with stirring for 1 hour at a hydrogen pressure of 2 MPa and at a reaction temperature of 60° C. As a result, the conversion of 3-hydroxypropionaldehyde was 98.8% and the selectivity of 1,3-propanediol was 100 mol %.

EXAMPLE 17

Hydrogenation reaction of 3-HPA was carried out under the same conditions as in Example 16 except that 0.3 g of a Raney nickel catalyst (NDHT-MO, containing 5.4% Al and 0.5% Mo) manufactured by Kawaken Fine Chemicals Co., Ltd was used. As a result, the conversion of 3-hydroxypropionaldehyde was 99.7% and the selectivity of 1,3-propanediol was 100 mol %.

EXAMPLE 18

Hydrogenation reaction of 3-HPA was carried out under the same conditions as in Example 16 except that 0.3 g of a nickel/silica-alumina catalyst (E22U; content of supported Ni 60%) manufactured by Nikki Chemical Co., Ltd was used. As a result, the conversion of 3-hydroxypropionaldehyde was 99.7% and the selectivity of 1,3-propanediol was 99.4 mol %.

INDUSTRIAL APPLICABILITY

In the process of the present invention, the selectivity of hydration reaction of acrolein is high, so that the hydration

TABLE 6

| | | Reaction conditions | | | | | |
|---|---|---|---|---|---|---|---|
| Example | Catalyst | Temperature (° C.) | Reaction time (Hr) | Amount of catalyst (g) | Amount of acrolein (g) | Amount of water (g) | Conversion rate of acrolein (%) | Selectivity of 3-HPA (mol %) |
| Example 13 | SAPO-34/alumina | 60 | 4 | 10 | 7.5 | 30 | 62 | 92 |
| Example 14 | Ferrierite/alumina | 60 | 4 | 10 | 7.5 | 30 | 71 | 88 |
| Comparative Example 6 | TP-208 | 60 | 0.75 | 13.8 (ml) | 7.5 | 30 | 60 | 79 |

EXAMPLE 15

Fifty grams of catalyst L prepared in Example 13 was packed in a 1-inch reactor (material: SUS316) with a jacket. A 15% by weight aqueous acrolein solution was introduced in a material container cooled at 5° C. and the starting material was fed into the reactor from above at a flow rate of 25 g/hr by the use of a pump. The temperature of the catalyst bed was maintained at 60° C. by passing hot water through the jacket of the reactor. The pressure was maintained at about 0.2 MPa in terms of gauge pressure. The product flowing out from the lower part of the reactor was periodically sampled, and then analyzed in the same manner as in Example 1.

The reaction results are shown in Table 7. It can be seen from Table 7 that catalyst L exhibits stable catalytic activity.

TABLE 7

| Hour of sampling (hr) | 19 | 235 | 304 |
|---|---|---|---|
| Conversion rate of acrolein (%) | 48 | 45 | 46 |
| Selectivity of 3-HPA (mol %) | 92 | 92 | 92 | product, 3-hydroxypropanal, can be obtained in high yield, and 1,3-propanediol important as a starting material for polyester or polyurethane can be obtained in high yield by hydrogenating the 3-hydroxypropanal. Therefore, said process is industrially very useful.

What is claimed is:

1. A process for producing 1,3-propanediol, comprising:

hydrating acrolein in a liquid phase in the presence of a hydration catalyst to form 3-hydroxypropanal;

separating any unreacted acrolein, if any is present; and carrying out catalytic hydrogenation of the 3-hydroxypropanal in a liquid or gas phase with a hydrogenation catalyst, wherein the hydration catalyst is a catalyst comprising at least one member selected from the group consisting of the following materials (a) to (c) and has a pH of 6 or less at 20° C., when made into a slurry by dispersing the catalyst in a quantity of water 5 tim s as much as the quantity of catalyst by weight ratio:

(a) a metalloaluminophosphate molecular sieve, (b) a FER type zeolite, and (c) an oxide or compound oxide, excluding crystalline aluminosilicate zeolites, which comprises one or more element(s) selected from the elements belonging to group 4, group 13 and group 14 of the periodic table, and the oxide or mixed oxide is one obtained by contacting the oxide or compound oxide with one or more acids selected from the group consisting of sulfuric acid and monobasic acids and washing with water until the washings become free of acid(s).

2. The process according to claim 1, wherein the metalloaluminophosphate molecular sieve is a silicoaluminophosphate molecular sieve.

3. The process according to claim 2, wherein the silicoaluminophosphate molecular sieve is SAPO-34.

4. The process according to claim 2, wherein the silicoaluminophosphate molecular sieve is SAPO-11.

5. The process according to claim 1, wherein the FER type zeolite is ferrierite.

6. A process for producing 1,3-propanediol, comprising:

hydrating acrolein in a liquid phase in the presence of a hydration catalyst to form 3-hydroxypropanal;

separating any unreacted acrolein, if any is present; and carrying out catalytic hydrogenation of the 3-hydroxypropanal in a liquid or gas phase with a hydrogenation catalyst, wherein the hydration catalyst is a catalyst comprising at least one member selected form the group consisting of the following materials (a) to (c) and has a pH of 6 or less at 20° C., when made into a slurry by dispersing the catalyst in a quantity of water 5 times as much as the quantity of catalyst by weight ratio:

(a) a metalloaluminophosphate molecular sieve, (b) a FER type zeolite, and (c) alumina.

7. A process for producing 1,3-propanediol, comprising:

hydrating acrolein in a liquid phase in the presence of a hydration catalyst to form 3-hydroypropanal;

separating an unreacted acrolein, if an is resent; and carrying out catalytic hydrogenation of the 3-hydroxypropanal in a liquid or gas phase with a hydrogenation catalyst, wherein the hydration catalyst is a catalyst comprising at least one member selected form the group consisting of the following materials (a) to (c) and has a pH of 6 or less at 20° C., when made into a slurry by dispersing the catalyst in a quantity of water 5 times as much as the quantity of catalyst by weight ratio:

(a) SAPO-34 or SAPO-11

(b) ferrierite, and (c) alumina.

8. The process according to any one of claims 1 to 5, 6 and 7, wherein the hydration reaction is carried out at a reaction temperature of 20 to 200° C. and a weight ratio of acrolein to water of 1:2 to 1:20.

9. The process according to any one of claims 1 to 5, 6 and 7, wherein the catalytic hydrogenation of the 3-hydroxypropanal is carried out at a temperature of 30–200° C. and a pressure of 1–20 MPa in the presence of a catalyst containing nickel or a noble metal.

10. The process according to claim 1, wherein the oxide is alumina.

11. The process according to claim 8, wherein the catalytic hydrogenation of the 3-hydroxypropanal is carried out at a temperature of 30–200° C. and a pressure of 1–20 MPa in the presence of a catalyst containing nickel or a noble metal.

12. The process according to claim 10, wherein the hydration reaction is carried out at a reaction temperature of 20 to 200° C. and a weight ratio of acrolein to water of 1:2 to 1:20.

13. The process according to claim 10, wherein the catalytic hydrogenation of the 3-hydroxypropanal is carried out at a temperature of 30–200° C. and a pressure of 1–20 MPa in the presence of a catalyst containing nickel or a noble metal.

* * * * *